United States Patent [19]

Monfardini et al.

[11] Patent Number: 5,021,054
[45] Date of Patent: Jun. 4, 1991

[54] EXTRAFOCAL FIXING APPARATUS FOR TRANSOSTEAL SYNDESIS OF STRAINS AND COMPRESSIONS IN ORTHOPEDICS AND TRAUMATOLOGY

[75] Inventors: Alessio Monfardini; Angelo Grassi, both of Palazzolo sull'Oglio, Italy

[73] Assignee: Ortomedical S.r.l., Palazzolo sull'Oglio, Italy

[21] Appl. No.: 495,180

[22] Filed: Mar. 19, 1990

[30] Foreign Application Priority Data

Mar. 22, 1989 [IT] Italy ................... 19859 A/89

[51] Int. Cl.⁵ ................................. A61F 5/04
[52] U.S. Cl. ................................. 606/54; 606/56; 606/57; 606/59
[58] Field of Search ................... 606/53–59

[56] References Cited

U.S. PATENT DOCUMENTS

| | | | |
|---|---|---|---|
| 2,014,638 | 9/1935 | Scofield | 606/59 |
| 2,346,346 | 4/1944 | Anderson | 606/59 |
| 2,391,693 | 12/1945 | Ettinger | 606/59 |
| 2,557,364 | 6/1951 | Treace | 606/53 |
| 4,677,972 | 7/1987 | Tornier | 606/53 |
| 4,890,631 | 1/1990 | Hardy | 606/59 |
| 4,893,618 | 1/1990 | Herzberg | 606/54 |
| 4,920,959 | 5/1990 | Witzel | 606/53 |
| 4,923,458 | 5/1990 | Fischer | 606/59 |

Primary Examiner—Robert A. Hafer
Assistant Examiner—Michael Brown
Attorney, Agent, or Firm—Guido Modiano; Albert Josif

[57] ABSTRACT

Extrafocal fixing apparatus for transosteal syndesis of strains and compressions in orthopedics and traumatology which includes rectilinear and curved rod-like elements which can be coupled to one another through clamps which define seats for the removable accommodation of the rod-like elements to be mutually secured. The clamps have a single securing element which acts on the rod-like elements arranged in the seats. Mandrels are furthermore provided for supporting tensioned wires and supporting bars and are removably accommodatable in the seats of the clamps and can be secured through the securing elements.

15 Claims, 3 Drawing Sheets

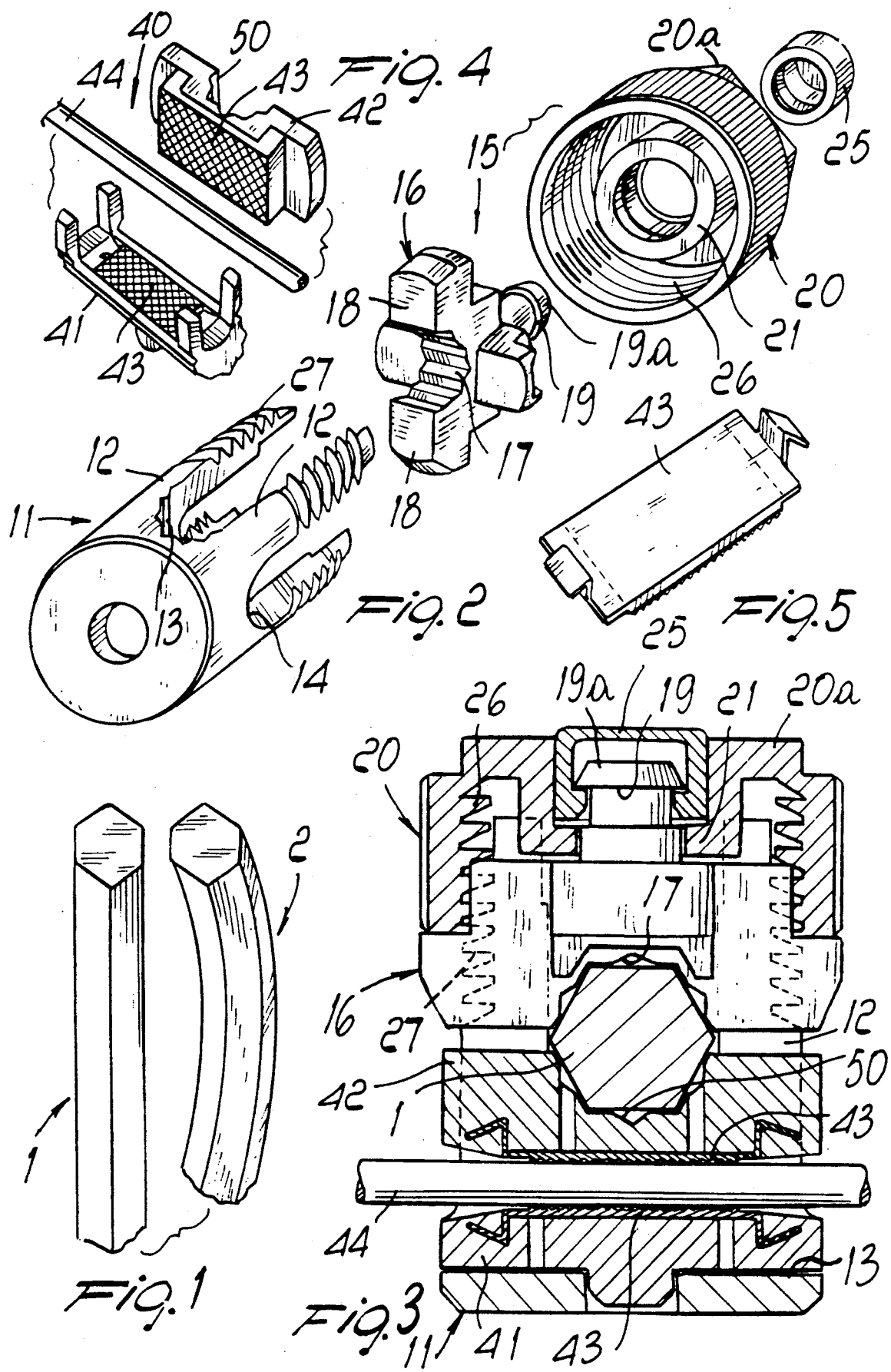

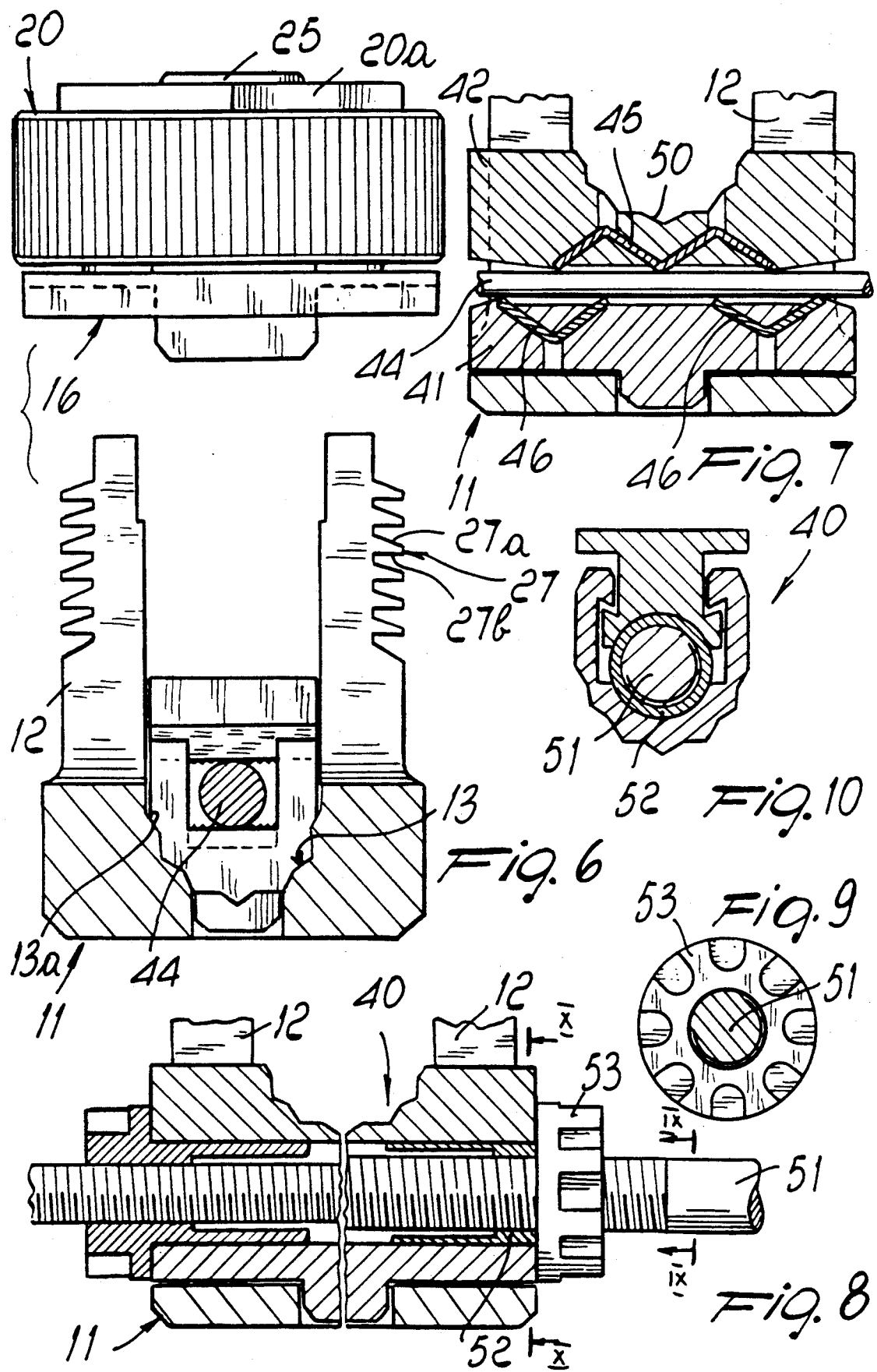

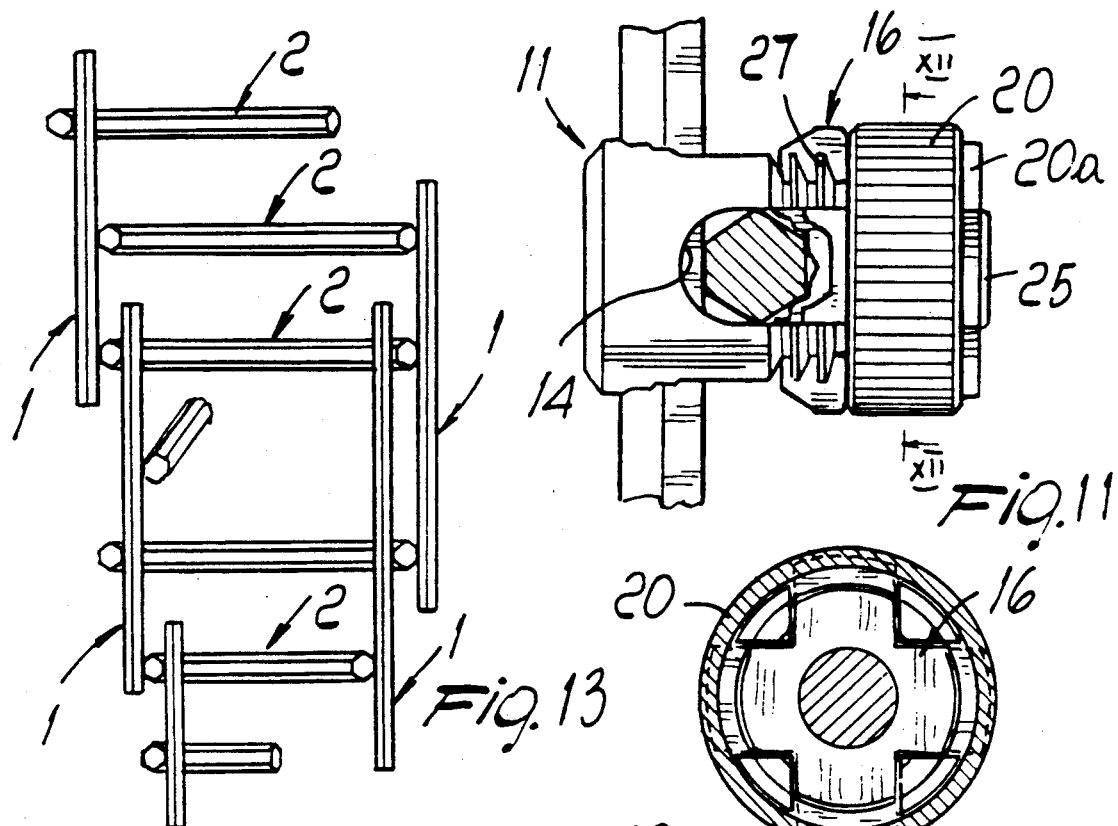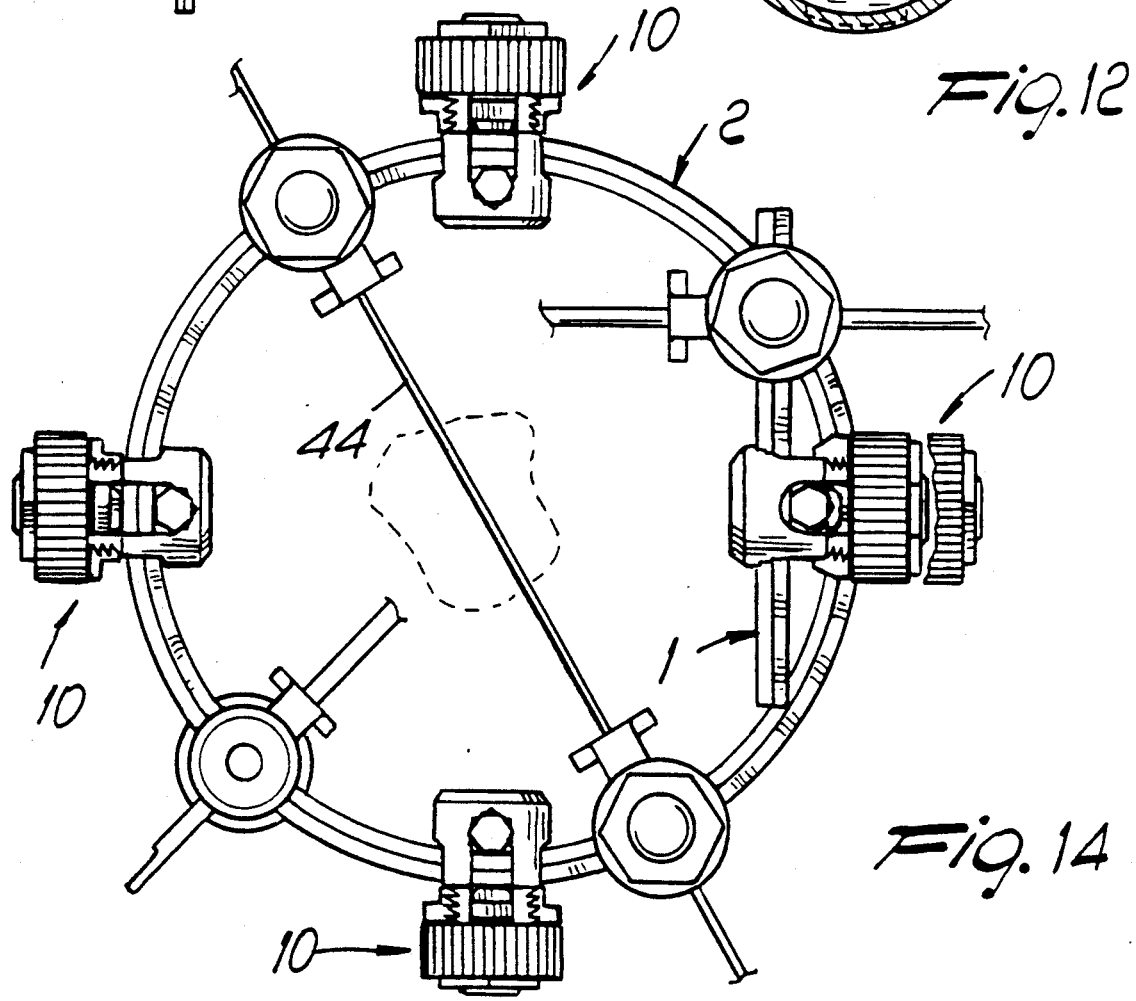

5,021,054

EXTRAFOCAL FIXING APPARATUS FOR TRANSOSTEAL SYNDESIS OF STRAINS AND COMPRESSIONS IN ORTHOPEDICS AND TRAUMATOLOGY

BACKGROUND OF THE INVENTION

The present invention relates to an extrafocal fixing apparatus for transosteal syndesis of strains and compressions in orthopedics and traumatology.

As is known, for anatomical reduction of bone lesions with high stability fixing of the bone stumps, and for preservation of the supporting and locomotor functions of the damaged limb, including early mobilization of the patient and for other orthopedic and traumatological treatments, devices are currently used which generally have a supporting frame constituted by rectilinear and curved rods which are mutually coupled; transosteal wires are then coupled to the frame and exert the required supporting action.

Known devices of this kind are constituted by an extremely large number of elements, and in particular the various elements are coupled with means which are structurally complicated and laborious to operate; said couplings are in fact performed by means of bolts, washers, bushes, nuts and the like, i.e. with a purely mechanical apparatus which requires, for the correct fixing of the elements, considerably long intervention times caused by the need to connect the elements to one another.

Another disadvantage is due to the fact that the entire apparatus is made of metallic material, which creates difficulties at a later time since it can be detected in radiographs and consequently does not allow to satisfactorily point out the fractures and bone regions to be treated, as radiographic observation of the frame can create dark areas indeed in the regions where the maximum possible clarity would be necessary.

Still another disadvantage is due to the fact that known apparata are constituted by a large number of component elements which, by virtue of their particular structure, can create difficulties in the necessary sterilization steps previous to their application.

SUMMARY OF THE INVENTION

The aim of the invention is indeed to eliminate the above described disadvantages by providing an extrafocal fixing apparatus for transosteal syndesis of strains and compressions in orthopedics and traumatology which allows to obtain an almost infinite range of configurations and structures, starting from a considerably simplified number of component elements, and which can be easily and rapidly assembled without requiring, at least in the initial step, the use of particular tools for fixing.

Within the scope of the above described aim, a particular object of the invention is to provide an apparatus in which a single securing element is provided and can be used on all the components of the system, with the consequent possibility of drastically reducing intervention times and increasing ease in operation.

Another object of the present invention is to provide an apparatus which is made of radiotransparent materials, especially in the parts which define the so-called supporting framework, thus contributing to an easier visualization of the bone region on which it is necessary to intervene, since said framework does not negatively affect radiographs.

A further object of the present invention is to provide an apparatus in which the elements can be manually secured to each other at an initial step and only subsequently should be locked by means of a single tool which is standard for all the component elements.

Not least object of the present invention is to provide an apparatus which is structurally simple and which is furthermore capable of giving the greatest assurances of reliability and safety in use.

The above described aim, as well as the objects mentioned and others which will become apparent hereinafter, are achieved by an extrafocal fixing apparatus for transosteal syndesis of strains and compressions in orthopedics and traumatology, as defined in the appended claims.

BRIEF DESCRIPTION OF THE DRAWINGS

The characteristics and advantages will become apparent from the description of a preferred but not exclusive embodiment of an extrafocal fixing apparatus for transosteal syndesis of strains and compressions in orthopedics and traumatology, illustrated only by way of non-limitative example in the accompanying drawings, wherein:

FIG. 1 is a schematic, merely exemplifying view of a rectilinear rod-like element and of a curved rod-like element;

FIG. 2 is an exploded perspective view of a clamp;

FIG. 3 is a sectional view of a clamp taken along a diametrical plane;

FIG. 4 is a schematic view of a supporting element for a tensioned wire;

FIG. 5 is a view of the plate-like insert of a supporting mandrel;

FIG. 6 is a partially sectional exploded view of a securing element;

FIG. 7 is a view of a securing mandrel with an insert with shaped laminas;

FIG. 8 is a sectional view of a wire tensioning mandrel;

FIG. 9 is a sectional view taken along the line IX—IX of FIG. 8;

FIG. 10 is a sectional view of a mandrel taken along the line X—X of FIG. 8;

FIG. 11 is a schematic view of a clamp which joins two rod-like elements;

FIG. 12 is a sectional view taken along the line XII—XII of FIG. 11;

FIG. 13 is a schematic view of a possible arrangement of the rod-like elements for providing a supporting frame;

FIG. 14 is a schematic view of a supporting frame to which the clamps both for supporting the mandrels and for the mutual coupling of the rod-like elements are applied.

DESCRIPTION OF THE PREFERRED EMBODIMENTS

With reference to the above figures, the extrafocal fixing apparatus for transosteal syndesis of strains and compressions in orthopedics and traumatology, which will be briefly termed external fixing device hereafter, has rectilinear rod-like elements, indicated by 1, and curved rod-like elements 2 which can have the configuration of a circle or of a portion of circumference.

An important characteristic is constituted by the fact that the rod-like elements are made of a technoplastic material having the following characteristics:

| rectilinear rod-like elements | |
|---|---|
| density | 1.32–1.36 kg/dm$^3$ |
| flexural strength | 2100–2300 kg/cm$^2$ |
| compressive strength | 1700–1900 kg/cm$^2$ |
| traction resistance | 1500–1700 kg/cm$^2$ |
| curved rod-like elements | |
| density | 1.13–1.17 kg/dm$^3$ |
| flexural strength | 1000–1200 kg/cm$^2$ |
| compressive strength | 750–850 kg/cm$^2$ |
| traction resistance | 900–1100 kg/cm$^2$ |

Said rod-like elements can be placed in an autoclave for sterilization at 110°–130° C. without suffering technical deterioration and can be used, when installed, at temperatures comprised between −25° and 60° C.

Said rod-like elements can have any cross section deemed appropriate, though a transverse cross section substantially in the shape of a regular hexagon has been shown to be advantageous by experimental tests.

The rectilinear rod-like elements and the curved rod-like elements can have different dimensions so as to provide the coupling characteristics deemed optimal.

In order to assemble the rod-like elements 1 and 2 and the other components which will be described hereinafter, clamps, generally indicated by the reference numeral 10, are provided, comprising a fork-like body 11 defined by four lateral tines 12 protruding symmetrically from the bottom of the fork-like body 11 and delimiting a first seat, generally indicated at 13, and a second seat, indicated at 14, said seats 13, 14 being arranged at different distances from the bottom of body 11 and extending along substantially perpendicular directions.

With the above described arrangement of the seats, which are delimited by the tines 12, two rectilinear or curved rod-like elements which extend mutually perpendicular may be inserted in the fork-like body 11.

A securing presser pad, indicated at 15, is provided, which advantageously has a cross-shaped body 16 with a recess 17 delimited by protrusions 18 which must be arranged correspondingly to the second seat 14, so as to close said seat and obtain the mutual securing of the component elements, as will become apparent hereinafter.

If the cross-shaped body 16 is not inserted correctly, the presser pad 15 would protrude excessively with respect to the fork-shaped body and consequently would not allow securing.

A securing knob 20 is axially provided, on its inner bottom, with a bush 21 intended to accommodate an axial tang 19 which protrudes from the cross-shaped body 16 and can be secured in place by means of a snap-action cap 25 which inserts in a corresponding recess of the bush 21 and engages the frustum-shaped expansion 19a of the tang 19, thus joining the presser pad 15 and the knob 20 to one another, though said knob 20 can be rotated.

The knob 20 has, on its inner surface, a thread 26 which engages teeth 27 defined on the tines 12.

As is better shown in FIG. 6, said teeth 27 have a particular configuration: specifically, they have an inclined portion 27a directed toward the free end of the tines 12 and a planar portion 27b which is substantially perpendicular to the axis of the fork-shaped body 11.

A precise meshing with the thread 26 having a complementary shape is thus achieved and allows to exert very high securing forces.

In particular, the fact is stressed that the elements inserted in the seats 13 and 14 are secured simply by acting on the knob 20, with mutual securing.

Mandrels, which are generally indicated by the reference numeral 40 and may have different configurations, are insertable in the seat 13 or first seat to support the tensioned wires and the supporting bars.

As illustrated in FIG. 4, the mandrels 40 comprise a lower body 41 and an upper body 42 which can be mutually associated and have knurled plates 43 for retaining the tensioned wire 44 which is clamped therebetween.

The upper body 42 defines, on its face which is directed toward the seat 14 of the fork-like body 11, a recess 50 which in practice arranges itself at the second recess defining seat 14.

The knurled metallic plates 43 are advantageously of the kind sunk in the supporting bodies 41 and 42.

According to FIG. 7, the mandrel, still generally indicated by the reference numeral 40, has retention inserts defined by shaped laminas 45 and 46 which again engage the tensioned wire 44.

According to a different embodiment of the mandrel, again indicated by 40, it is possible to provide a threaded bar 51 which is accommodated in threaded bushes 52 contained inside the mandrel 40. An adjustment ring 53 is provided externally and allows to perform precise axial positioning (see FIGS. 8–10).

In order to achieve the required angular orientation of the clamp and of the various mandrels or inserts which are applied, the first seat 13 defined on the fork-like body 11 advantageously has, in transverse cross section, a step-like configuration, indicated by 13a, and a similar step-like configuration can be found on the lower body of the mandrels 40 and on the recess defined by the presser element.

In this manner, by using bars with hexagonal cross section, it is possible to obtain twelve continuous angular positions.

Said twelve different angular positions are obviously indicated merely as a preferential and non-limitative number, since they could be varied in any way and be replaced with almost infinite angles by using circular cross sections.

With the described arrangement, the various clamps can be manually tightened by exerting an appropriate grip during preassembly and positioning of the various component elements and only subsequently make it possible to secure them by means of a torque wrench or other similar element which engages a polygonal portion 20a defined at one axial end of the knob 20.

By using the above described clamp, all the operations for applying the fixing device and any corrections or operations for removal from the patient are considerably facilitated and expedited.

The cross-like shape of the presser pad and the appropriate coupling tolerances among the eight inner faces between the tines of the fork-like body and of the cross-shaped body ensure considerable rigidity, preventing the inward bending of said tines during the screwing of the securing knob or ring.

The four free ends of the tines of the fork-like body are furthermore comprised between the bush 21 and the threaded inner surface of the knob 20, thus obtaining a cylindrical abutment seat which ensures additional rigidity for said tines during final locking.

As previously mentioned, the body of the clamps is completely radiotransparent, whereas the small metallic inserts which are provided on the mandrels for gripping the tensioned wires of the supporting and positioning bars do not hinder radiological detections since the metallic parts are always arranged at the wires or at the bars, which are metallic.

With the above described apparatus it is consequently possible to fit and lock the wires and/or bars on the ring-shaped, circular or rectilinear rod-like elements, with the angle deemed most appropriate, with no restrictions at all for correct positioning.

From what has been described it can thus be seen that the invention achieves the proposed aim and objects, and in particular the fact is stressed that the reduced number of types of component elements and their geometrical unification allows, while preserving a very high versatility in use, to reduce the assembly tool kit to a single multiple wrench or to a single torque wrench.

The wires can be fitted, tensioned and locked on the ring, passing diametrically through the center for the ring, or off-center in a chord-like manner; one, two or more ring wires can be furthermore fitted above or below the ring on planes which are parallel or oblique with respect to the plane of said ring.

The wires can furthermore be fitted by connecting two supporting bars of the framework which are diametrically opposite or arranged in a chord-like manner, by connecting rectilinear and/or curved or circular segments mounted on the supporting bars or on the rings, on planes which are parallel to the planes of the rings and/or on planes which can even be sharply oblique to said planes of the rings.

The bars can be fitted and locked on rings, bars, rectilinear and circular segments, on the same planes as the rings and/or on inclined planes, exactly like the wires.

The entire apparatus can be mounted with a single rectilinear axis, with broken and/or parallel axes, with rings of the same and/or different diameter, with rings on parallel and/or oblique planes.

The various rings and rods can furthermore be manufactured by means of portions provided with insertion joints which allow their mutual coupling, which can be stabilized by using one of the clamps; this aspect can be obtained because on the surface, in the region of fit between the various portions, there are no parts which protrude with respect to the cross section of the various portions.

All the elements which provide the supporting framework can furthermore be provided fully wrap-around, i.e. so as to completely surround the limb, or open at 90°-120°-180°; said framework can be mixed, i.e. with an open part and a closed part.

The invention thus conceived is susceptible to numerous modifications and variations, all of which are within the scope of the inventive concept.

All the details may furthermore be replaced with other technically equivalent elements.

In practice, though the best results have been obtained by using technoplastic materials, the materials employed, as well as the contingent shapes and dimensions, may be any according to the requirements.

We claim:

1. An extrafocal fixing apparatus for orthopedic use comprising rectilinear rod-like elements, curved rod-like elements, wire means, and clamp means for interconnecting said rod-like elements and wire means in said fixing apparatus, wherein said clamp means comprise a body means defining a longitudinal extension, said body means further defining body threaded means, said body threaded means being at least partially cylindrical body threaded means, said clamp means further comprising a securing knob means which define a knob threaded means, said knob threaded means being at least partially cylindrical knob threaded means which are threadingly engageable with said cylindrical body threaded means to allow an axial movement of said knob means relative to said longitudinal extension of said body means, said body means further defining a first seat means and a second seat means both transversing said body means and both extending substantially perpendicular to said body means longitudinal extension, said first seat means and said second seat means being arranged at different positions along said body means longitudinal extension, said first seat means and said second seat means extending along substantially mutual perpendicular directions, said clamp means further comprising a mandrel means being arranged between said first and second seat means and having first side and a second side, said first side of said mandrel means constituting at least a portion of said first seat means and said second side of said mandrel means constituting at least a portion of said second seat means, said clamp means further comprising a presser pad means which defines at one end a recess means which constitutes at least another portion of said second seat means, said knob means being provided with a bush means for acting on a second end of said presser pad means, said rod-like elements and said wire means being accommodatable in said seat means, whereby a loosened position of said knob means allows free movement of said rod-like elements and said wire means in said seat means and a tightening rotation of said knob means clamps said rod-like elements and said wire means in said seat means.

2. An apparatus according to claim 1, wherein said rectilinear and said curved rod-like elements and said clamp means are made of radiotransparent material, said rod-like elements having, in transverse cross-section, a substantially hexagonal configuration.

3. An extrafocal fixing apparatus for orthopedic use comprising rectilinear rod-like elements, curved rod-like elements, wire means, and clamp means for interconnecting said rod-like elements and wire means in said fixing apparatus, wherein said clamp means comprise a body means defining a longitudinal extension, said body means further defining body threaded means, said body threaded means being at least partially cylindrical body threaded means, said clamp means further comprising a securing knob means which define a knob threaded means, said knob threaded means being at least partially cylindrical knob threaded means which are threadingly engageable with said cylindrical body threaded means to allow an axial movement of said knob means relative to said longitudinal extension of said body means, said body means further defining a first seat means and a second seat means both transversing said body means and both extending substantially perpendicular to said body means longitudinal extension, said first seat means and said second seat means being arranged at different positions along said body means longitudinal extension, said first seat means and said second seat means extending along substantially mutual perpendicular directions, said clamp means further comprising a mandrel means being arranged between said first and second seat means and having a first side and a second side, said first side of said mandrel means constituting at least a portion of said first seat means and said second side of said mandrel means constituting at least a portion of said second seat means, said clamp means further comprising a presser pad means which defines at one end a recess means which constitutes at least another portion of said second seat means, said knob means being provided with a bush means for acting on a second end of said presser pad means, said rod-like elements and said wire means being accommodatable in said seat means, whereby a loosened position of said knob means allows free movement of said rod-like elements and said wire means in said seat means and a tightening rotation of said knob means clamps said rod-like elements and said wire means in said seat means, said body means being a fork-like body, said fork-like body defining a bottom from which four tines extend longitudinally, said tines delimiting therebetween said first and said second seat means along substantially mutually orthogonal directions, said body threaded means being defined on ends of said tines arranged away from said bottom.

4. An apparatus according to claim 3, wherein said mandrel means have an upper body and a lower body, said upper body of said mandrel means having said first side and said second side, said lower body being accommodated in said first seat means, said lower body and said first seat means having, in transverse cross-section, a step-like configuration at mutually engaged surfaces thereof so as to define a plurality of discrete positions for inclined orientation thereof.

5. An apparatus according to claim 4, wherein said lower body of said mandrel means defines a knurled-plate surface in said first seat means, said first side of said upper body also being a knurled-plate surface.

6. An apparatus according to claim 4, wherein said first side of said upper body of said mandrel means and said lower body are provided with retention inserts, said retention inserts being defined by shaped laminas.

7. An apparatus according to claim 4, wherein said mandrel means define threaded bushes arranged between said upper and lower bodies, a threaded bar being provided which is accommodatable in said threaded bushes and an adjustment ring being provided externally thereby allowing precise axial positioning of said threaded bar.

8. An apparatus according to claim 3, wherein said rectilinear and said curved rod-like elements and said clamp means are made of radiotransparent material, said rod-like elements having, in transverse cross-section, a substantially hexagonal configuration, said portion of said second seat means defined on said second side of said mandrel means and said recess means of said presser pad means having, in transverse cross-section, a step-like configuration so as to define a plurality of discrete positions for said hexagonal rod-like elements arrangeable therebetween.

9. An extrafocal fixing apparatus for orthopedic use comprising rectilinear rod-like elements, curved rod-like elements, wire means, and clamp means for interconnecting said rod-like elements and wire means in said fixing apparatus, wherein said clamp means comprise a body means defining a longitudinal extension, said body means further defining body threaded means, said body threaded means being at least partially cylindrical body threaded means, said clamp means further comprising a securing knob means which define a knob threaded means, said knob threaded means being at least partially cylindrical knob threaded means which are threadingly engageable with said cylindrical body threaded means to allow an axial movement of said knob means relative to said longitudinal extension of said body means, said body means further defining a first seat means and a second seat means both transversing said body means and both extending substantially perpendicular to said body means longitudinal extension, said first seat means and said second seat means being arranged at different positions along said body means longitudinal extension, said first seat means and said second seat means extending along substantially mutual perpendicular directions, said clamp means further comprising a mandrel means being arranged between said first and second seat means and having a first side and a second side, said first side of said mandrel means constituting at least a portion of said first seat means and said second side of said mandrel means constituting at least a portion of said second seat means, said clamp means further comprising a presser pad means which defines at one end a recess means which constitutes at least another portion of said second seat means, said knob means being provided with a bush means for acting on a second end of said presser pad means, said rod-like elements and said wire means being accommodatable in said seat means, whereby a loosened position of said knob means allows free movement of said rod-like elements and said wire means in said seat means and a tightening rotation of said knob means clamps said rod-like elements and said wire means in said seat means, said body means being a fork-like body, said fork-like body defining a bottom from which four tines extend longitudinally, said tines delimiting therebetween said first and said second seat means along substantially mutually orthogonal directions, said body threaded means being defined on ends of said tines arranged away from said bottom, said presser pad means being a cross-shaped body being insertable between said tines of said fork-like body, said cross-shaped body defining an axial tang opposite to said end at which said recess means is defined, said knob means being a cylindrical securing knob defining a knob bottom, said bush means being a cylindrical bush axially arranged inside said cylindrical securing knob at said knob bottom, said cylindrical securing knob having a cylindrical hole in said knob bottom extending through said cylindrical bush, said axial tang of said cross-shaped body being arrangeable through said cylindrical hole and defining an expansion being protrudable therefrom for engagement with a snap-lock cap thereby allowing free axial movement of said securing knob relative to said tang while also being secured thereto.

10. An apparatus according to claim 9, wherein said knob threaded means are knob threads defined on an inner lateral surface of said cylindrical knob, said body threaded means being a set of teeth defined on bends of said tines, each tooth of said set of teeth having, in transverse cross-section, an inclined portion directed toward a free end of said tines and a planar portion which is substantially perpendicular to a longitudinal axis of said fork-like body.

11. An apparatus according to claim 9, wherein said mandrel means have an upper body and a lower body, said upper body of said mandrel means having said first side and said second side, said lower body being accommodated in said first seat means, said lower body and said first seat means having, in transverse cross-section, a step-like configuration at mutually engaged surfaces thereof so as to define a plurality of discrete positions for inclined orientation thereof.

12. An apparatus according to claim 11, wherein said lower body of said mandrel means defines a knurled-plate surface in said first seat means, said first side of said upper body also being a knurled-plate surface.

13. An apparatus according to claim 11, wherein said first side of said upper body of said mandrel means and said lower body are provided with retention inserts, said retention inserts being defined by shaped laminas.

14. An apparatus according to claim 11, wherein said mandrel means define threaded bushes arranged between said upper and lower bodies, a threaded bar being provided which is accommodatable in said threaded bushes and an adjustment ring being provided externally thereby allowing precise axial positioning of said threaded bar.

15. An apparatus according to claim 9, wherein said rectilinear and said curved rod-like elements and said clamp means are made of radiotransparent material, said rod-like elements having, in transverse cross-section, a substantially hexagonal configuration.

* * * * *